United States Patent
LeGrow et al.

(10) Patent No.: US 7,235,230 B2
(45) Date of Patent: Jun. 26, 2007

(54) LEAVE-ON COMPOSITIONS FOR PERSONAL CARE

(75) Inventors: Gary E. LeGrow, Newberry, FL (US); W. Leonard Terry, Jr., Gainesville, FL (US); Ray Figueroa, Hollywood, FL (US); Peter Klug, Grossostheim (DE); Waltraud Simsch, Kelkheim (DE); Angelika Turowski, Kelkheim (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/002,710

(22) Filed: Oct. 24, 2001

(65) Prior Publication Data

US 2003/0086888 A1 May 8, 2003

(51) Int. Cl.
*A61K 7/11* (2006.01)
*A61K 7/00* (2006.01)
*A61K 31/74* (2006.01)

(52) U.S. Cl. ............... 424/70.121; 424/401; 424/78.03; 424/DIG. 2; 514/937

(58) Field of Classification Search ............ 424/70.121, 424/401, 78.03, 78.02, 70.1, 70.12, 70.15, 424/47, DIG. 1, DIG. 2
See application file for complete search history.

(56) References Cited

U.S. PATENT DOCUMENTS

| 3,755,560 | A | | 8/1973 | Dickert et al. |
|---|---|---|---|---|
| 4,254,105 | A | | 3/1981 | Fukuda |
| 4,421,769 | A | | 12/1983 | Dixon et al. |
| 4,919,934 | A | | 4/1990 | Deckner et al. |
| 4,937,370 | A | | 6/1990 | Sabatelli |
| 4,960,764 | A | | 10/1990 | Figueroa, Jr. et al. |
| 4,985,459 | A | | 1/1991 | Sunshine et al. |
| 4,999,186 | A | | 3/1991 | Sabatelli et al. |
| 5,011,681 | A | | 4/1991 | Ciotti et al. |
| 5,108,738 | A | * | 4/1992 | Halloran et al. ....... 424/70.121 |
| 5,628,989 | A | * | 5/1997 | Harashima et al. ........... 424/65 |
| 5,643,555 | A | * | 7/1997 | Collin et al. .................. 424/59 |
| 5,888,879 | A | * | 3/1999 | Nishikata et al. ........... 424/401 |
| 5,932,231 | A | | 8/1999 | LeGrow et al. |
| 6,143,309 | A | * | 11/2000 | Legrow et al. ............. 424/401 |

OTHER PUBLICATIONS

Title page for McCutcheon's Emulsifiers & Detergents, 1986, North America Edition, IDBN #0–944254–24–6.

Cosmetics & Toiletries, "Sun Products Formulary", vol. 102, Mar. 1987, p. 117–136.

Cosmetics & Toiletries, "Sun Products Formulary", vol. 105, Dec. 1990, p. 122–139.

* cited by examiner

Primary Examiner—Michael G. Hartley
Assistant Examiner—Blessing Fubara
(74) Attorney, Agent, or Firm—Anthony A. Bisulca

(57) ABSTRACT

The present invention relates to leave-on compositions for personal care comprising trimethylsilylalkylsilsesquioxanes, particularly trimethylsilyl-n-octylsilsesquioxanes (Caprylyl Trimethicones). Said trimethylsilylalkylsilsesquioxanes are especially useful in formulating emulsions.

17 Claims, No Drawings

LEAVE-ON COMPOSITIONS FOR PERSONAL CARE

The present invention relates to leave-on compositions for personal care comprising trimethylsilyl-alkylsilsesquioxanes, particularly trimethylsilyl-n-octylsilsesquioxanes (Caprylyl Trimethicones).

The present leave-on compositions have improved aesthetics and leave less visible (e.g. white) residue on the skin after application or after drying. They provide a good, non-oily skin feel, enhanced spreadability and lubricity, water repellency and reduced stickiness and tackiness.

Said trimethylsilyl-alkylsilsesquioxanes act in skin care products as a water barrier, leaving the skin soft and smooth and have utility in hair care to improve gloss and sheen.

The leave-on compositions can be used in different physical forms, including powders, suspensions, emulsions, structured solids, creams, soft solids, lotions, aerosol or pump sprays.

BACKGROUND OF THE INVENTION

The rheological and sensoric benefits and organic compatibility of silicone compounds have contributed immensely to their usefulness in a wide variety of personal care compositions, including skin creams, lotions, antiperspirants and deodorants, color cosmetics (e.g. mascara, lipstick) suncare products and hair conditioners.

A variety of patents describe various types of formulations based on silicone compounds, like dimethiconol, polyalkylsiloxanes, polyalkylarylsiloxanes, polyestersiloxanes, polyethersiloxanes, polyfluorosiloxanes, polyaminosiloxanes and combinations thereof. Especially, the use of dimethylsilicones, both linear and cyclic, provide desirable sensory benefits during application. Non-volatile silicones provide desirable sensory attributes to the hair and to the skin subsequent to the application. Unfortunately, dimethylsilicones show limited compatibility with many organic materials used in cosmetic formulations. Also they are generally not compatible with water.

Phenyltrimethicones, of the general formula $Me_3SiO[Si(Me_3SiO)(Ph)O]_xSiMe_3$, with x from 1 to 3, are a class of silicones which show excellent compatibility with many organic ingredients. Phenyltrimethicones are formulated into cosmetic products for a number of purposes including better gloss and sheen of hair, increased emolliency and water repellency of the skin. During the application of cosmetic products said phenyl trimethicones also provide enhanced spreadability and lubricity and reduced tackiness.

Considerable study has been carried out in recent years concerning the ultimate fate of organosilicones (atmosphere, rivers and lakes).

Phenyl substituents are oxidized and/or homolytically cleaved from silicon forming benzene and/or phenol. Both are considered to be pollutants of the environment.

DESCRIPTION OF THE PRESENT INVENTION

Surprisingly it was found by the applicant that trimethylsilyl-alkylsilsesquioxanes are particularly suitable to formulate leave-on compositions for personal care. Surprisingly said trimethylsilylalkylsilsesquioxanes increase considerably the gloss and sheen of the hair, increase considerably the emolliency and water repellency of the skin and show superior spreading. During application they provide enhanced spreadability and lubricity and reduced tackiness. Surprisingly the results are even better than those achieved with phenyltrimethicones.

Said trimethylsilylalkylsilsesquioxanes are particularly useful to formulate emulsions. Advantageously said trimethylsilyl-alkylsilsesquioxanes are environmentally friendly and show excellent compatibility with many organic materials used in cosmetic formulations.

Therefore, the present invention provides leave-on compositions for personal care comprising from 0.1 to 60% by weight of at least one trimethylsilylalkylsilsesquioxane of formula (1)

$$Me_3SiO—[Si(R)(Me_3SiO)O]_x—SiMe_3 \qquad (1)$$

wherein Me is methyl, and R is a straight or branched alkyl group having from 6 to 18 carbon atoms and x is a number from 1 to 10.

The alkyl groups R in formula (1) have preferably from 6 to 14 carbon atoms, particularly preferred are n-octyl groups —$C_8H_{17}$. x in formula (1) is preferably a number from 1 to 4, particularly preferred are compounds wherein x equals 1.

Surprisingly it has been found that trimethylsilylalkylsilsesquioxanes of formula (1) which are substantially free of alkoxysilanes, chlorosilanes, silanol functionalities and organic and/or inorganic compounds are particularly useful for the present invention.

Preferred are the trimethylsilylalkylsilsesquioxanes which contain less than 3% by weight, more preferred less than 1% by weight, of alkoxysilanes, chlorosilanes, silanol functionalities and organic and/or inorganic compounds.

Such high purity trimethylsilyl-alkylsilsesquioxanes of formula (1) can be prepared according to the process described in U.S. Pat. No. 5,932,231 by hydrolyzing a mixture of pure trimethylchlorosilane and pure alkyltrichlorosilane having from 6 to 18, preferably 6 to 14, carbon atoms with distilled water in an amount sufficient to produce an aqueous layer of less than about 25 weight percent hydrochloric acid, maintaining the temperature of the hydrolysis reaction mixture below about 90° C., to form a silicone intermediate; washing residual acid from the silicone reaction intermediate; and azeotropically removing water from the washed silicone intermediate to produce a dried silicone reaction intermediate; and trimethylsilylating the silanol groups in the dried silicone reaction intermediate with at least a stoichiometric amount of hexamethyldisiloxane in the presence of an acid catalyst.

All the embodiments of the process described in U.S. Pat. No. 5,932,231 are hereby incorporated by reference into the description of the present application.

The leave-on compositions preferably comprise from about 0.1% to 60% by weight, more preferred from 0.5% to 10% by weight, particularly preferred from 1% to 5% by weight of trimethylsilylalkylsilsesquioxanes.

In a preferred embodiment the leave-on compositions of the present invention comprise further volatile silicone derivatives (especially siloxanes such as alkylheptamethyltrisiloxanes, octamethylcyclotetrasiloxane, decamethylcyclopentasiloxane, cyclomethicones, and dimethicones, preferably such having a viscosity of 5 centipoise or less at 25° C.) and hydrophobically modified silicones or mixtures thereof having the formula (2)

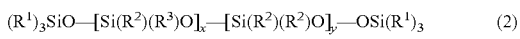
$$(R^1)_3SiO—[Si(R^2)(R^3)O]_x—[Si(R^2)(R^2)O]_y—OSi(R^1)_3 \qquad (2)$$

wherein $R^1$ is a $(C_1-C_{20})$-alkyl group, $R^2$ is a $(C_1-C_4)$-alkyl group, $R^3$ is a $(C_2-C_{25})$-alkyl group and x has a number average value in the range of from about 20 to 400, y has a number average value in the range of from about 0 to about 10 and x+y lies in the range of 30 to 400.

Leave-on Compositions:

The trimethylsilylalkylsilsesquioxanes can be formulated into a wide variety of leave-on compositions for personal care, like lotions, creams, ointments, gels, tonics, sprays, aerosols, conditioners, hand and body lotions, facial moisturizers, solid gel sticks, sunscreens, anti-acne preparations, topical analgesics, mascaras, makeups, antiperspirants and deodorants. Preferably the leave-on compositions are topical skin care or hair care compositions.

Emulsions as Preferred Embodiments:

Surprisingly it has also been found that the trimethylsilyl-alkylsilsesquioxanes of formula (1) are particularly useful for formulating leave-on compositions which are emulsions, preferably oil-in-water type emulsions, triple emulsions and microemulsions. It has been found that emulsions comprising trimethylsilylalkylsilsesquioxanes, particularly caprylyl trimethicones, show superior performance concerning the smoothness, tackiness and emolliency compared to phenyltrimethicones. Also the trimethylsilylalkyl-silsesquioxanes show superior emulsion stability compared to dimethylpolysiloxanes (dimethicones) (see examples A to E).

The above findings are very surprising in view of the teaching of U.S. Pat. No. 5,932,231 which teaches equal sensory characteristics for caprylyltrimethicones and phenyltrimethicones when compared as pure oil phases.

Preferably the leave-on compositions are topical skin care or hair care compositions.

Topical Skin Care Compositions:

The topical cosmetic compositions of the present invention can comprise a carrier. The carrier should be "cosmetically and/or pharmaceutically acceptable", which means that the carrier is suitable for topical application to the skin, has good aesthetic properties and is compatible with other components.

Said carriers can be present from about 5 to 99% by weight of the compositions of the present invention, more preferably from about 50 to about 99% by weight, and most preferably from about 85 to 95% by weight. The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems): and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" Cosmetics & Toiletries, vol. 105, pp. 122–139 (December 1990); "Sun Products Formulary", Cosmetics & Toiletries, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

Hair Care Compositions:

The hair care compositions of the present invention can comprise a carrier, or a mixture of such carriers, which are suitable for application to the hair. The carriers are preferably present at from about 0.5 to 99.5% by weight, preferably from about 1.0 to 99.5% by weight, more preferably from about 5.0 to 98.0% by weight, of the compositions. As used herein, the phrase "suitable for application to hair" means that the carrier does not damage or negatively affect the aesthetics of hair or cause irritation to the underlying skin.

Carriers suitable for use with hair care compositions of the present invention include those used in the formulation of hair sprays, mousses, tonics and gels. The choice of appropriate carriers will also depend on the particular trimethylsilyl-alkylsilsesquioxane to be used, and whether the product formulated is meant to be left on the surface to which it is applied (e.g., hair spray, mousse, tonic, or gel).

The carriers used herein can include a wide range of components conventionally used in hair care compositions. The carriers can contain a solvent to dissolve or to disperse additional copolymers being used. Water, $(C_1–C_6)$-alcohols and mixtures thereof being preferred, particularly preferred alcohols are methanol, ethanol and isopropanol. The carriers can also contain a wide variety of additional materials including acetone, hydrocarbons (such as isobutane, hexane, decane), halogenated hydrocarbons (such as Freons), linalool and esters (such as ethyl acetate, dibutyl phthalate). When the hair care composition is a hair spray, tonic, gel, or mousse the preferred solvents include water, ethanol, volatile silicone derivatives and mixtures thereof. The solvents used in such mixtures may be miscible or immiscible with each other. Mousses and aerosol hair sprays can also utilize any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilize an emulsifying agent. Examples of suitable emulsifying agents include nonionic, cationic, anionic surfactants, or mixtures thereof. Fluorosurfactants are especially preferred, particularly if the product is a hair spray composition and most especially if it is a spray composition having relatively low levels of volatile organic solvents, such as alcohols, and relatively high levels of water (e.g., in excess of 10% by weight water). If such an emulsifying agent is used, it is preferably present at a level of from about 0.01 to 7.5% by weight of the composition. The level of propellant can be adjusted as desired but is generally from about 3 to 30% by weight of mousse compositions and from about 15 to 70% by weight of the aerosol hair spray compositions.

Preferred cosmetically and/or pharmaceutically acceptable topical carriers include hydro-alcoholic systems and oil-in-water emulsions. When the carrier is a hydro-alcoholic system, the carrier can comprise from about 1 to about 50% by weight of ethanol, isopropanol, or mixtures thereof, and from about 40 to about 99% by weight of water. More preferred is a carrier comprising from about 5 to about 60% by weight of ethanol, isopropanol, or mixtures thereof, and from about 40 to about 95% by weight of water. Especially preferred is a carrier comprising from about 20 to about 50% by weight of ethanol, isopropanol, or mixtures thereof, and from about 50 to about 80% by weight of water. When the carrier is an oil-in-water emulsion, the carrier can include any of the common excipient ingredients for preparing these emulsions. Additional components useful in formulating these topical compositions are further described below.

Emulsifiers are useful for emulsifying the various carrier components of the compositions herein, and are not required for solubilizing or dispersing the copolymers of the present invention. Suitable emulsifiers can include any of a wide variety of nonionic, cationic, anionic, and zwitterionic emulsifiers disclosed in the prior patents and other references. See McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate. PEG-100 stearate, and mixtures thereof.

The compositions according to the present invention can also comprise lipophilic emulsifiers as skin care actives. Suitable lipohilic skin care actives include anionic food grade emulsifiers which comprise a di-acid mixed with a monoglyceride such as succinylated monoglycerides, monostearyl citrate, glyceryl monostearate diacetyl tartrate and mixtures thereof.

Preferably the present compositions comprise from 0.1 to 10% by weight, more preferably from 1 to 7% by weight, most preferably from 1 to 5% by weight, of emulsifiers.
Additional Components:

A wide variety of additional components can be employed in the leave-on compositions of the present invention.
Pharmaceutical Actives:

The compositions of the present invention, especially the topical skin care compositions, can comprise a safe and effective amount of a pharmaceutical active.

The pharmaceutical actives which can be used in the compositions of the present invention preferably comprise from 0.1 to 20% by weight of the compositions, more preferably from 0.1 to 10% by weight, most preferably from 0.1 to 5% by weight. Mixtures of pharmaceutical actives may also be used. Nonlimiting examples of pharmaceutical actives include the following:

Useful pharmaceutical actives in the compositions of the present invention include anti-acne actives. Anti-acne actives preferred for use in the present invention include the keratolytics such as salicylic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate, and cholate. Preferred for use herein is salicylic acid. Useful pharmaceutical actives in the compositions of the present invention include analgesic actives. Analgesic actives suitable for use in the present compositions include salicylic acid derivatives such as methyl salicylate, species and derivatives of the genus capsicum such as capsaicin and non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like. Useful pharmaceutical actives in the compositions of the present invention include antipruritic drugs. Antipruritic actives preferred for inclusion in compositions of the present invention include pharmaceutically-acceptable salts of methdilizine and trimeprazine. Useful pharmaceutical actives in the compositions of the present invention include anesthetic actives. Anesthetic actives preferred for inclusion in compositions of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine and pramoxine. Useful pharmaceutical actives in the compositions of the present invention include antimicrobial actives (antibacterial, antifungal, antiprotozoal and antiviral drugs). Antimicrobial actives preferred for inclusion in compositions of the present invention include pharmaceutically-acceptable salts of b-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole.

Also useful herein are sunscreening agents, like 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyidibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening actives disclosed therein have, in a single molecule, two distinct chromophore moieties which exhibit different ultra-violet radiation absorption spectra. One of the chromophore moieties absorbs pre-dominantly in the UVB radiation range and the other absorbs strongly in the UVA radiation range. These sunscreening actives provide higher efficacy, broader UV absorption, lower skin penetration and longer lasting efficacy relative to conventional sunscreens. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the sunscreens can comprise from about 0.5 to about 20% by weight of the compositions useful herein.

Also useful in the present invention are sunless tanning actives including dihydroxyacetone, glyceraldehyde, indoles and their derivatives, and the like. These sunless tanning actives may also be used in combination with the sunscreen agents.

Other useful actives include skin bleaching (or lightening) actives including but not limited to hydroquinone, ascorbic acid, kojic acid and sodium metabisulfite.

Other useful actives which are especially useful for hair care compositions include anti-dandruff actives such as zinc pyrithione, octopirox, selenium disulfide, sulfur, coal tar, and the like.

Other useful actives include antiperspirant actives. Suitable for use herein are those which comprise any compound, composition or mixture thereof having antiperspirant activity. Astringent metallic salts are preferred antiperspirant materials for use herein, particularly the inorganic and organic salts of aluminum, zirconium and zinc, as well as mixtures thereof. Particularly preferred are the aluminum and zirconium salts, such as aluminum halides, aluminum hydroxy halides, zirconyl oxide halides, zirconyl hydroxy halides, and mixtures thereof.

Additionally, deodorant actives in the form of bacteriostats may be incorporated into the present compositions. Suitable deodorant bacteriostats include 2,2'-methylenebis (3,4,6-trichlorophenol), 2,4,4'-trichloro-2'-hydroxy (diphenyl ether), zinc phenolsulfonate, 2,2'-thiobis(4,6-dichlorophenol), p-chloro-m-xylenol, dichloro-m-xylenol and the like. Most preferred is 2,4,4'-trichloro-2'-hydroxy (diphenyl ether), which is generically known as triclosan and available from the Ciba-Geigy Corporation under the trademark, Irgasan DP-300 Registered TM. When triclosan is utilized it will be present in a range from about 0.05 to about 0.9%, preferably from about 0.1 to about 0.5% by weight of the composition. Other types of bacteriostats include sodium N-lauroyl sarcosine, sodium N-palmitoyl sarcosine, lauroyl sarcosine, N-myristoyl glycine, potassium N-lauroyl sarcosine and aluminum chlorhydroxy lactate (sold by Reheis Chemical Company under trademark of Chloracel).

Conditioners:

Conditioning agents useful herein, and especially useful for hair care compositions, include hydrocarbons, silicone fluids, and cationic materials.

The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Silicone conditioning agents useful herein can include cyclic or linear polydimethylsiloxanes, phenylsilicone, alkylphenylsilicones, and silicone copolyols. The linear volatile silicones generally have viscosities of less than about 5 centistokes at 25° C., while the cyclic materials have viscosities less than about 10 centistokes.

Cationic conditioning agents useful herein include quaternary ammonium salts or the salts of fatty amines. These additional cationic agents are used herein for the purpose of providing conditioning and are separate and apart from the complexing agents of the present invention. Preferred quaternary ammonium salts are dialkyl dimethyl ammonium chlorides, wherein the alkyl groups have from 12 to 22 carbon atoms and are derived from long-chain fatty acids. Representative examples of quaternary ammonium salts include ditallow dimethyl ammonium chloride, ditallow dimethyl ammonium methyl sulfate, dihexadecyl dimethyl ammonium chloride, and di(hydrogenated tallow) ammonium chloride. Other quaternary ammonium salts useful herein are dicationics such as tallow propane diammonium dichloride. Quaternary imidazolinium salt are also useful herein. Examples of such materials are those imidazolinium salts containing ($C_{12}$–$C_{22}$) alkyl groups such as 1-methyl-1-(stearoylamide)ethyl-2-heptadecyl4,5-dihydroimidazolinium chloride, 1-methyl-1-(palmitoylamide)ethyl!-2-octadecyl-4,5-dihydroimidazolinium chloride and 1-methyl-1-(tallowamide)-ethyl-2-tallow-imidazolinium methyl sulfate. Also useful herein are salts of fatty amines. Examples of such compounds include stearylamine hydrochloride, soyamine hydrochloride, and stearylamine formate.

Humectants and Moisturizers:

The compositions of the present invention can contain one or more humectant or moisturizing materials. A variety of these materials can be employed and each can be present at a level of from about 0.1 to 20% weight, more preferably from 1 to 10% by weight and most preferably from 2 to 5% by weight. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine: and mixtures thereof. Preferred humectants and moisturizers are glycerol, butylene glycol, hexylene glycol, and mixtures thereof.

The compositions according to the present invention can optionally include a polymeric cationic conditioning agent. Polymeric conditioning agents are valuable in the compositions according to the present invention for provision of desirable skin feel attributes. The polymeric skin conditioning agent is preferably present at a level from 0.01 to 5% by weight, preferably from 0.01 to 3% by weight and especially from 0.01 to 2% by weight.

Suitable polymers are guar gums, cationic polysaccharides, cationic homopolymers and copolymers derived from acrylic and/or methacrylic acid, cationic cellulose resins, quaternized ethyl cellulose ethers, cationic copolymers of dimethyldiallylammonium chloride and acrylamide and/or acrylic acid, cationic homopolymers of dimethyldiallylammonium chloride, copolymers of dimethyl aminoethylmethacrylate and acrylamide, acrylic acid/dimethyldiallylammonium chloride/acrylamide copolymers, quaternized vinyl pyrrolidone acrylate or methacrylate copolymers of amino alcohol, quaternized copolymers of vinyl pyrrolidone and dimethylaminoethylmethacrylamide, vinyl pyrrolidone/vinyl imidazolium methochloride copolymers and polyalkylene and ethoxypolyalkylene imines, terpolymers of acrylic acid, methacrylamidipropyl trimethyl ammonium chloride and methyl acrylate and mixtures thereof.

The compositions of the invention may also contain from about 0.1 to 20% by weight, preferably from about 1 to 15% by weight and more preferably from about 2 to about 10% by weight of an oil derived nonionic surfactant or mixture of oil derived nonionic surfactants. Oil derived nonionic surfactants are valuable in compositions according to the invention for the provision of skin feel benefits both in use and after use. Suitable oil derived nonionic surfactants for use herein include water soluble vegetable and animal-derived emollients such triglycerides with a polyethyleneglycol chain inserted, ethoxylated mono- and di-glycerides, polyethoxylated lanolins and ethoxylated butter derivatives. Suitable ethoxylated oils and fats of this class include polyethylenglycol, derivatives of glyceryl cocoate, glyceryl caproate, glyceryl caprylate, glyceryl tallowate, glyceryl plamate, glyceryl stearate, glyceryl laurate, glyceryl oleate, glyceryl ricinoleate and glyceryl fatty esters derived from triglycerides, such as palm oil, almond oil and corn oil, preferably glyceryl tallowate and glyceryl cocoate.

Other suitable oil-derived nonionic surfactants include ethoxylated derivatives of almond oil, peanut oil,rice bran oil, wheat germ oil, linseed oil, jojobaoil, oil of apricot pits, walnuts, palm nuts, pstachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

The compositions useful in the methods of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 1 to 50% by weight, preferably from 1 to 25% by weight, and more preferably from 1 to 10% by weight of the compositions useful in the present invention.

The compositions herein can additionally comprise water-insoluble polyalphaolefin oils, such polymers of butene, isoprene, terpene, styrene or isobutene.

Another water-insoluble skin/hair care ingredient suitable for use in the foaming compositions herein is a liquid polyol carboxylic acid ester.

The preferred liquid polyol polyesters employed in this invention comprise certain polyols, such as erythritol, xylitol, sorbitol, glucose, sucrose, especially sugars or sugar alcohols, monosaccharides, such xylose, arabinose, disaccharides, esterfied with at least four fatty acid groups.

In addition the compositions of the invention may also include an insoluble perfume or cosmetic oil or wax or a mixture thereof at a level up to 10% by weight, preferably up to 3% by weight wherein the oil or wax is insoluble in the sense of beeing insoluble in the product matrix at a temperature of 25° C.

Suitable insoluble cosmetic oils and waxes for use herein can be selected from water-insoluble silicones inclusive of non-volatile polyalkyl and polyaryl siloxane gums and fluids, volatile cyclic polydimethylsiloxanes, polyalkoxylated silicones, amino and quaternary ammonium modified silcones, rigid cross-linked and reinforced silcones and mixtures thereof, $(C_1-C_{24})$ esters of $(C_8-C_{30})$-fatty acids such as isopropyl myristate, myristyl myristate and cetyl ricinoleate, $(C_8-C_{30})$-esters of benzoic acid, beeswax saturated and unsaturated fatty alcohols such as behenyl alcohol, hydrocarbons such as mineral oils, petrolatum, squalane and squalene, fatty sorbitan esters, lanolin and oil-like lanolin derivatives, animal and vegetable triglycerides such as almond oil, peanut oil, wheat germ oil, rice bran oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soyabean oil, avocado oil, safflower oil, coconut oil, hazelnut oil, olive oil, grapeseed oil, sunflower seed oil, $(C_1-C_{24})$-esters of dimer and trimer acids such as diisopropyl dimerate, diisostearylmalate, diisostearyldimerate and triisostearyltrimerate.

The compositions herein may also include one or more suspending agents. Suitable suspending agents for use herein include any of several long chain acyl derivative materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to 22 carbon atoms, preferably from about 16 to 18 carbon atoms. Preferred alkanol amides are stearic monoethanolamide, stearic diethanolamide, stearic monoisopropanolamide and stearic monoethanolamide stearate.

Compositions according to the invention may so include an opacifier or pearlescing agent. Such materials may be included at a level from 0.01 to 5% by weight, preferably from about 0.2 to 1.3% by weight.

Opacifiers/pearlescers suitable for inclusion in the compositions of the present invention include: titanium dioxide, $TiO_2$, EUPERLAN 810® (RTM); TEGO-PEARL® (RTM); long chain $(C_{16}-C_{22})$-acyl derivatives such as glycol or polyethylene glycol esters of fatty acid having from about 16 to about 22 carbon atoms and up to 7 ethyleneoxy units; alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide and alkyl $(C_{16}-C_{22})$ dimethyl oxides such as stearyl dimethyl amine oxide.

In preferred compositions the opacifier/pearlescer is present in the form of crystals. In highly preferred compositions the opacifier/pearlescer is a particulate polystyrene dispersion having a particle size from about 0.05 microns to about 0.45 microns, preferably from about 0.17 microns to about 0.3 microns, such dispersions being preferred from the viewpoint of providing optimum rheology and shear-thinning behaviour. Highly preferred is styrene acrylate copolymer and OPACFIER 680® (RTM) commercially available from Morton International.

The pH of the compositions is preferably from 3 to 10, more preferably from 3.5 to 9, especially from 4.8 to 8 and most preferably from 5 to 7.

Also subject-matter of the present invention is a process for increasing the gloss and sheen of hair, wherein said process comprises applying an effective amount of a leave-on composition comprising from 0.1 to 60% by weight of at least one trimethyl-silylalkylsilsesquioxane of formula (1)

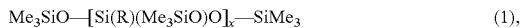

$$Me_3SiO-[Si(R)(Me_3SiO)O]_x-SiMe_3 \qquad (1),$$

wherein Me is methyl, and R is a straight or branched alkyl group having from 6 to 18 carbon atoms and x is a number from 1 to 10, to said hair.

In a further aspect, the present invention provides processes for increasing the emolliency and for increasing the water repellency of the skin, wherein said process comprises applying an effective amount of a leave-on composition comprising from 0.1 to 60% by weight of at least one trimethylsilylalkyl-silsesquioxane of formula (1)

$$Me_3SiO-[Si(R)(Me_3SiO)O]_x-SiMe_3 \qquad (1),$$

wherein Me is methyl, and R is a straight or branched alkyl group having from 6 to 18 carbon atoms and x is a number from 1 to 10, to said skin.

Trimethyl-silylalkylsilsesquioxanes of formula (1) particularly preferred for use in the above three processes are those already described in the present application.

EXAMPLES

The following examples further illustrate preferred embodiments within the scope of the present invention. The examples are given solely for the purposes of illustration and are not to be construed as limitations of the present invention as many variations of the invention are possible without departing from its spirit and scope. Ingredients are identified by chemical or CTFA name.

Example 1

Anhydrous Stick

| Ingredients | % w/w | Trade name | Supplier |
|---|---|---|---|
| Phase A | | | |
| Stearyl alcohol | 22.30 | Codacol S-95 | Croda |
| (C$_{24}$–C$_{28}$)-Alkyl dimethicone | 10.00 | SilCare 41M80 | Clariant |
| Tribehenin and Calcium Behenate | 7.50 | Syncrowax HRS-C | Croda |
| PPG-2 Myristyl Ether Propionate | 5.00 | Crodamol PMP | Croda |
| Paraffin | 3.00 | Paraffin 201 | Koster Keunen |
| Phase B | | | |
| Caprylyl Trimethicone | 52.00 | SilCare 31M30 | Clariant |
| Fragrance | 0.20 | | |

Manufacturing Procedure:

1. Heat Phase A to 90–95° C. Mix well.
2. Initiate slow cooling. Mix and add Phase B.
3. Mix and cool to 40° C. Add fragrance.

Example 2

Antifriz Hair Gel

| Ingredients | % w/w | Trade name | Supplier |
|---|---|---|---|
| Phase A | | | |
| Dipropylene glycol | 40.00 | Dipropylene glycol | Arco |
| Distilled water | 25.30 | Water | N/A |
| Phase B | | | |
| Caprylyl Trimethicone | 8.00 | SilCare 31M60 | Clariant |
| Caprylyl Trimethicone | 7.00 | SilCare 31M50 | Clariant |
| Phase C | | | |
| Dimethicone | 1.60 | SE-30 | Gen. Electric |
| Caprylyl Trimethicone | 14.40 | SilCare 31M30 | Clariant |
| Phase D | | | |
| Polyacrylamide, Laureth-7 and C$_{13}$–C$_{14}$ Isoparaffin | 2.50 | Sepigel 305 | Seppic |
| Phase E | | | |
| Iodopropynyl Butylcarbamate | 1.00 | Jeecide IPBC, 10% | Jeen Int |

Manufacturing Procedure:

1. Combine ingredients of Phase A
2. Combine ingredients of Phase B
3. Solubilize Dimethicone in Capryl trimethicone
4. Mix Phase A, B and C
5. Under vigorous mixing, add Sepigel 305 and mix until the product is uniform and lump-free
6. Add Ingredients of Phase E with mixing within 2–3 minutes

Example 3

Diaper Rash Cream

| Ingredients | % w/w | Trade name | Supplier |
|---|---|---|---|
| Phase A | | | |
| deionized water | Q.S. | N/A | N/A |
| Sodium chloride FCC | 0.60 | Sodium chloride | various |
| Phenoxyethanol and Methylparaben and Ethylparaben and Butylparaben and Propylparaben and Isopropylparaben | 0.25 | Phenonip | Clariant |
| Phase B | | | |
| Caprylyl Trimethicone | 5.00 | SilCare 31M30 | Clariant |
| White petrolatum USP | 4.50 | Ultrapure SC | Ultra |
| Stearoxytrimethylsilane | 3.00 | SilCare 1M71 | Clariant |
| Stearyl Dimethicone | 1.50 | SilCare 41M65 | Clariant |
| Ethylhexyl Stearate | 5.00 | Tegosoft OS | Goldschmidt |
| Light Mineral Oil NF | 4.00 | Ultrasol 70 | Ultra |
| Polyglyceryl-6 Isostearate | 0.50 | Plurol Isostearique | Gattefosse |
| Hydrogenated Castor Oil | 0.80 | Cutina HR | Cognis |
| White Beeswax NF | 1.20 | Beeswax | Hansotech |
| Phase C | | | |
| Fragrance | 0.25 | | |

Manufacturing procedure:

1. Heat Phase A to 50–55° C.
2. Heat Phase B to 80–85° C.
3. Emulsify adding slowly Phase A to Phase B. Mix at high speed to emulsify. Cool to 50° C.

4. Mix and cool below 35° C. Homogenize to obtain a smooth cream.
5. While slowly mixing add fragrance. Mix for 3–5 minutes.

Example 4

Moisturizer

| Ingredients | % w/w | Trade name | Supplier |
|---|---|---|---|
| Phase A | | | |
| Cetyl Dimethicone Copolyol | 2.00 | Abil EM 90 | Goldschmidt |
| Mycrocrystalline Wax | 1.40 | SP-89 | Sthrals&Pitsch |
| Hydrogenated Castor Oil | 1.00 | Hansonwax JH80 | Hanson |
| Caprylic/Capric Triglyceride | 8.00 | Labrafac WL1349 | Gattefosse |
| Octyl Palmitate | 4.00 | Trivent OP | Trivent |
| Decyl Oleate | 4.00 | Cetyol V | Cognis |
| Phase B | | | |
| Caprylyl Trimethicone | 10.00 | SilCare 31M50 | Clariant |
| Phase C | | | |
| Deionized Water | 60.90 | N/A | N/A |
| Sodium Chloride | 0.50 | N/A | N/A |
| Urea | 2.00 | Urea | E M Ind |
| SD Alcohol 40B | 5.00 | Alcohol | Local |

Manufacturing procedure:
1. Heat Phase A to 50–55° C.
2. Heat Phase B to 80–85° C.
3. Emulsify adding slowly Phase A to Phase B. Mix at high speed to emulsify. Cool to 50° C.
4. Mix and cool below 35° C. Homogenize to obtain a smooth cream.
5. Whlie slowly mixing add fragrance. Mix for 3–5 minutes.

Example 5

Sunscreen Cream

| Ingredients | % w/w | Trade name | Supplier |
|---|---|---|---|
| Phase A | | | |
| Deionized Water | 60.64 | N/A | N/A |
| Glycerin, USP | 5.00 | Glycerin | Local |
| Carbomer | 0.40 | Carbopol Ultrez 10 | BFGoodrich |
| Disodium EDTA | 0.50 | Dissolvine NA2 | AKZO |
| Phase B | | | |
| Sodium Hydroxide | 0.40 | Sodium Hydroxide | JT Baker |
| Phase C | | | |
| Cetyl Alcohol, And Ceteh-20 and Steareth-20 | 2.00 | Emulsire 61 WL | Gattefosse |
| Glyceryl Stearate | 5.00 | Lipomulse 165 | Lipo |
| Cetyl Alcohol, NF | 0.50 | Crodacol C-95 | Croda |
| Stearyl Alkohol, NF | 1.50 | Crodacol S-95 | Croda |
| Caprylyl Trimethicone | 7.50 | Silcare 31M50 | Clariant |
| Isostearyl Isostearate | 4.00 | Isos. D'isostearyle | Gattefosse |
| Octyl Methoxycinnamate | 7.50 | Parsol MCX | Roche |
| Butyl Methoxydibenzoyl- | 1.50 | Parsol 1789 | Roche |
| Butylated hydroxytoluene | 0.01 | BHT | Clariant |
| Phase D | | | |
| Hexyl Methicone | 2.25 | Silcare 41M10 | Clariant |

-continued

| Ingredients | % w/w | Trade name | Supplier |
|---|---|---|---|
| Dimethicone | 0.25 | SE-30 | Gen. Electric |
| Phase E | | | |
| Iodopropynyl-Butylcarbamate | 1.00 | Jeecide IPBC, 10% | Jeen Int |
| Fragrance | 0.50 | | |

Manufacturing procedure
1. Disperse Carbomer in Water. Heat this dispersion to 75–80° C. Add Glycerin and Disodium EDTA.
2. After dissolution of the EDTA; continue mixing and add sodium hydroxide, 20% solution.
3. Separately, heat Phase C to 75–80° C. Then add to Phase (A+B).
4. Continue mixing and cool to 40–45° C.
5. Solubilize dimethicone in hexyl methicone. Then add to batch.
6. Continue mixing and cool to 35° C. Add phase E ingredients.
7. Mix to uniformity

Example 6

Waterproof Sunscreen Spray Mist

| Ingredients | % w/w | Trade name | Supplier |
|---|---|---|---|
| Phase A | | | |
| Anhydrous Ethanol SDA 3A | 64.20 | SDA 3A | Various |
| Deionized Water | Q.S. | N/A | N/A |
| Acrylates/Octylacrylamide | 1.00 | Dermacryl 79 LT | Natl. Starch |
| Phase B | | | |
| Octyl Methoxycinnamate | 7.50 | Parsol MCX | Roche |
| Benzophenone-3 | 3.00 | Escalol 567 | ISP |
| Methyl Anthranilate | 3.50 | Dermablock | Alzo |
| Caprylyl Methicone | 5.00 | SilCare 31M50 | Clariant |
| $(C_{12}-C_{15})$-Alkylbenzoate | 10.00 | Finsolv TN | Finetex |
| Butylated hydroxytoluene | 0.02 | BHT | Clariant |
| Propylparaben | 0.10 | Nipasol | Clariant |
| Vitamin E | 0.25 | Vitamin E | Protameen |
| Phase C | | | |
| Fragrance | 0.50 | | |

Manufacturing Procedure:
1. Mix water and ethanol. Disperse slowly Dermacryl. Mix to clarity.
2. Add one by one ingredients of Phase B, mix until clear.
3. Add fragrance. Mix until clear.

Example 7

Antiperspirant Cream

| Ingredients | % w/w | Trade name | Supplier |
|---|---|---|---|
| Phase A | | | |
| Cetyl alcohol | 2.5 | Crodacol C-95 | Croda |
| Stearyl alcohol | 2.5 | Crodacol S-95 | Croda |
| Aluminium Chlorohydrate | 10.0 | Locron P | Clariant |

-continued

| Ingredients | % w/w | Trade name | Supplier |
|---|---|---|---|
| Oleth-10 and Oleth-5 | 3.0 | Emulgin M8 | Sidobre Sinnova |
| Phase B | | | |
| Cyclomethicone | 9.0 | Belsil CM 040 | Wacker |
| Caprylyl Methicone | 3.0 | SilCare 31M50 | Clariant |
| Deionized Water | 63.4 | N/A | N/A |
| Fragrance | q.s. | | |
| Pigments | q.s. | | |

Manufacturing Procedure:
1. Mix A and heat to 70° C.
2. Heat water to 70° C. and add to A
3. Add silicones
4. Add fragrance and pigments Example 8

Antiperspirant Stick

| Ingredients | % w/w | Trade name | Supplier |
|---|---|---|---|
| Phase A | | | |
| Caprylyl Trimethicone | 15.30 | Silcare 31 M 30 | Clariant |
| Stearyl Alcohol | 36.70 | Crodacol S-95 | Croda |
| Dicaprylyl Carbonate | 22.90 | Cetiol CC | Clariant |
| Sorbitan Stearate | 2.10 | Arlacel 60 | |
| Phase B | | | |
| Aluminium Chlorohydrate | 23.00 | Locron P | Clariant |

Manufacturing Procedure:
1. Melt the components of A at about 70° C.
2. While stirring add B into A.
3. Cool down to about 50° C. and fill in stick Example 9

O/W Cream

| Ingredients | % w/w | Trade name | Supplier |
|---|---|---|---|
| Phase A | | | |
| Polyglyceryl-2 Sesquiisostearate | 2.00 | Hostacerin DGI | Clariant |
| Caprylyl Trimethicone | 2.00 | SilCare 31M30 | Clariant |
| Perliquidum | 6.00 | Paraffin oil | Various |
| Octyldodecanol | 4.00 | Eutanol G | Henkel |
| Isopropylpalmitate | 4.00 | | Various |
| Carbomer | 0.70 | Carbopol 980 | Clariant |
| Phase B | | | |
| Sodium Cocoylglutamate | 0.60 | Hostapon KCG | Clariant |
| Causic soda (10% in H2O) | 2.10 | | Various |
| Preservative | q.s. | | |
| Perfume | 0.40 | | |
| Deionized Water | ad 100 | | |

Manufacturing Procedure
1. Heat Phase A to 80° C.
2. Heat Phase B to 80° C.
3. Add slowly phase B to phase A. Mix at high speed to emulsify. 4. Homogenize to obtain a smooth cream.

Examples A to E

Comparison of Caprylyl Trimethicones vs:Phenyl Trimethicones/Dimethicones

Examples A, B and C

Example A

Sprayable Antiperspirant Emulsion Containing Caprylyl Trimethicone

| Ingredients | % w/w | Trade name | Supplier |
|---|---|---|---|
| Phase A | | | |
| Stearyeth-20 | 2.00 | Genapol HS 200 | Clariant |
| PEG-40 hydrogenated Castor Oil | 2.00 | Emulsogen HCO 040 | Clariant |
| Polyglyceryl-2 Sesquiisostearate | 2.00 | Hostacerin DGI | Clariant |
| CaprylylTrimethicone | 0.40 | SilCare 31M50 | Clariant |
| Dicapryl Ether | 5.00 | Cetiol OE | Cognis |
| Coco Caprylate Caprate | 5.00 | Cetiol LC | Cognis |
| Phase B | | | |
| Water | ad 100 | | |
| Aluminium Chlorohydrate | 10.00 | LOCRON LIC | Clariant |
| Phase C | | | |
| Fragrance | 0.30 | | |
| Preservative | q.s. | | |

Manufacturing procedure:
1. Melt A at approx. 60° C.
2. Heat B to approx. 60° C.
3. Add B to I while stirring
4. At 35° C. add C to I Example B Sprayable Antiperspirant Emulsion Containing Phenyl Trimethicone

| Ingredients | % w/w | Trade name | Supplier |
|---|---|---|---|
| Phase A | | | |
| Stearyeth-20 | 2.00 | Genapol HS 200 | Clariant |
| PEG-40 hydrogenated Castor Oil | 2.00 | Emulsogen HCO 040 | Clariant |
| Polyglyceryl-2 Sesquiisostearate | 2.00 | Hostacerin DGI | Clariant |
| Phenyltrimethicone | 0.40 | SilCare 15M50 | Clariant |
| Dicapryl Ether | 5.00 | Cetiol OE | Cognis |
| Coco Caprylate Caprate | 5.00 | Cetiol LC | Cognis |
| Phase B | | | |
| Water | ad 100 | | |
| Aluminium Chlorohydrate | 10.00 | LOCRON LIC | Clariant |
| Phase C | | | |
| Fragrance | 0.30 | | |
| Preservative | q.s. | | |

Manufacturing procedure:
1. Melt A at approx. 60° C.
2. Heat B to approx. 60° C.
3. Add B to I while stirring
4. At 35° C. add C to I

Example C

Sprayable Antiperspirant Emulsion Containing Dimethicone

| Ingredients | % w/w | Trade name | Supplier |
|---|---|---|---|
| Phase A | | | |
| Stearyeth-20 | 2.00 | Genapol HS 200 | Clariant |
| PEG-40 hydrogenated Castor Oil | 2.00 | Emulsogen HCO 040 | Clariant |
| Polyglyceryl-2 Sesquiisostearate | 2.00 | Hostacerin DGI | Clariant |
| Dimethicone 50 cSt | 0.40 | Dow Corning 200 | Dow Corning |
| Dicapryl Ether | 5.00 | Cetiol OE | Cognis |
| Coco Caprylate Caprate | 5.00 | Cetiol LC | Cognis |
| Phase B | | | |
| Water | ad 100 | | |
| Aluminium Chlorohydrate | 10.00 | LOCRON LIC | Clariant |
| Phase C | | | |
| Fragrance | 0.30 | | |
| Preservative | q.s. | | |

Manufacturing procedure:

1. Melt A at approx. 60° C.
2. Heat B to approx. 60° C.
3. Add B to I while stirring
4. At 35° C. add C to I The stability of examples A, B and C was evaluated after 2 weeks storage at 25° C. Examples A and B were still stable, whereas example C showed phase seperation.

Sensory assessment of emulsions A, B and C were done with a trained sensory panel. Tackiness (during drying on skin) and smoothness (in the dry state) were assessed on a scale from 1 to 5 (1=bad, 5=excellent).

Tackiness and smoothness of examples A, B and C to skin:

| Example | tackiness | smoothness |
|---|---|---|
| A | 4 | 5 |
| B | 2 | 3 |
| C | 3 | 4 |

As a result Caprylyl Trimethicones (example A) showed superior sensoric behaviour over Phenyl Trimethicones (example B) and Dimethicones (example C). Additionally Caprylyl Trimethicones (example A) show superior compatibility compared to Dimethcones (C) and increased formulation stability.

Examples D and E

Example D

O/W Cream Containing Caprylyl Trimethicone

| Ingredients | % w/w | Trade name | Supplier |
|---|---|---|---|
| Phase A | | | |
| Polyglyceryl-2 Sesquiisostearate | 2.00 | Hostacerin DGI | Clariant |
| Caprylyl Trimethicone | 2.00 | SilCare 31M30 | Clariant |
| Perliquidum | 6.00 | Paraffin oil | Various |
| Octyldodecanol | 4.00 | Eutanol G | Cognis |
| Isopropylpalmitate | 4.00 | | Various |
| Carbomer | 0.70 | Carbopol 980 | Clariant |
| Phase B | | | |
| Sodium Cocoylglutamate | 0.60 | Hostapon KCG | Clariant |
| causic soda (10% in H$_2$O) | 2.10 | | Various |
| Preservative | q.s. | | |
| Perfume | 0.40 | | |
| Deionized Water | ad 100 | | |

Manufacturing Procedure:

1. Heat Phase A to 80° C.
2. Heat Phase B to 80° C.
3. Emulsify adding slowly Phase B to Phase A. Mix at high speed to emulsify. C. Homogenize to obtain a smooth cream.

Example E

O/W Cream Containing Phenyl Trimethicone

| Ingredients | % w/w | Trade name | Supplier |
|---|---|---|---|
| Phase A | | | |
| Polyglyceryl-2 Sesquiisostearate | 2.00 | Hostacerin DGI | Clariant |
| Phenyl Trimethicone | 2.00 | SilCare 15M30 | Clariant |
| Perliquidum | 6.00 | Paraffin oil | Various |
| Octyldodecanol | 4.00 | Eutanol G | Cognis |
| Isopropylpalmitate | 4.00 | | Various |
| Carbomer | 0.70 | Carbopol 980 | Clariant |
| Phase B | | | |
| Sodium Cocoylglutamate soda (10% in H$_2$O) | 0.60 2.10 | Hostapon KCG | Clariant causic Various |
| Preservative | q.s. | | |
| Perfume | 0,40 | | |
| Deionized Water | ad 100 | | |

Manufacturing Procedure:

1. Heat Phase A to 80° C.
2. Heat Phase B to 80° C.
3. Add slowly phase B to phase A. Mix at high speed to emulsify. Homogenize to obtain a smooth cream.

Sensory assessment of the Emulsions D and E were done with a trained sensory panel. Tackiness (during drying on skin) and smoothness (in the dry state) were assessed on a scale from 1 to 5 (1=bad, 5=excellent).

Tackiness and smoothness of examples D and E to skin:

| Example | tackiness | smoothness |
|---------|-----------|------------|
| D | 4 | 5 |
| E | 2 | 2 |

As a result Caprylyl Trimethicones also showed improved sensory assessment in skin creams compared to Phenyl Trimethicones.

What is claimed is:

1. Leave-on composition for personal care comprising from 0.1 to 60% by weight of at least one trimethylsilylalkyl-silsesquioxane of formula (1)

$$\text{Me}_3\text{SiO}-[\text{Si}(R)(\text{Me}_3\text{SiO})\text{O}]_x-\text{SiMe}_3 \quad (1)$$

wherein Me is methyl, and R is a straight or branched alkyl group having from 6 to 18 carbon atoms and x is a number from 1 to 10, wherein the leave-on composition is an emulsion.

2. Leave-on composition according to claim 1, wherein R in formula (1) is an alkyl group having from 6 to 14 carbon atoms.

3. Leave-on composition according to claim 2, wherein R in formula (1) is a n-octyl group.

4. Leave-on composition according to claim 1, wherein x in formula (1) is a number from 1 to 4.

5. Leave-on composition according to claim 4, wherein x in formula (1) is equal 1.

6. Leave-on composition according to claim 1, wherein the trimethylsilylalkylsilsesquioxanes of formula (1) are substantially free of alkoxysilanes, chlorosilanes, silanol functionalities and organic and/or inorganic compounds.

7. Leave-on composition according to claim 6, wherein the trimethylsilylalkylsilsesquioxanes of formula (1) contain less than 3% by weight of alkoxysilanes, chlorosilanes, silanol functionalities and organic and/or inorganic compounds.

8. Leave-on compositions according to claim 1, wherein they comprise from 0.5% to 10% by weight of trimethylsilylalkyl-silsesquioxanes of formula (1).

9. Leave-on composition according to claim 1 which is a topical skin care or a hair care product.

10. Leave-on composition according to claim 1, which is an oil-in-water emulsion.

11. Leave-on composition according to claim 1 which is a microemulsion.

12. Leave-on composition according to claim 1 which is a triple emulsion.

13. Process for increasing the gloss and sheen of hair, wherein said process comprises applying an effective amount of a leave-on composition comprising from 0.1 to 60% by weight of at least one trimethylsilylalkylsilsesquioxane of formula (1)

$$\text{Me}_3\text{SiO}-[\text{Si}(R)(\text{Me}_3\text{SiO})\text{O}]_x-\text{SiMe}_3 \quad (1)$$

wherein Me is methyl, and R is a straight or branched alkyl group having from 6 to 18 carbon atoms and x is a number from 1 to 10, to said hair wherein the leave-on composition is an emulsion.

14. Process for increasing the emolliency of the skin, wherein said process comprises applying an effective amount of a leave-on composition comprising from 0.1 to 60% by weight of at least one trimethylsilylalkylsilsesquioxane of formula (1)

$$\text{Me}_3\text{SiO}-[\text{Si}(R)(\text{Me}_3\text{SiO})\text{O}]_x-\text{SiMe}_3 \quad (1),$$

wherein Me is methyl, and R is a straight or branched alkyl group having from 6 to 18 carbon atoms and x is a number from 1 to 10, to said skin, wherein the leave-on composition is an emulsion.

15. Process for increasing the water repellency of the skin, wherein said process comprises applying an effective amount of a leave-on composition comprising from 0.1 to 60% by weight of at least one trimethylsilylalkylsilsesquioxane of formula (1)

$$\text{Me}_3\text{SiO}-[\text{Si}(R)(\text{Me}_3\text{SiO})\text{O}]_x-\text{SiMe}_3 \quad (1),$$

wherein Me is methyl, and R is a straight or branched alkyl group having from 6 to 18 carbon atoms and x is a number from 1 to 10, to said skin, wherein the leave-on composition is an emulsion.

16. Leave-on composition according to claim 6, wherein the trimethylsilylalkylsilsesquioxanes of formula (1) contain less than 1% by weight of alkoxysilanes, chlorosilanes, silanol functionalities and organic and or inorganic compounds.

17. Leave-on compositions according to claim 1, comprising from 1% to 5% by weight of trimethylsilylalkyl-silsesquioxanes of formula (1).

* * * * *